US011737795B1

(12) United States Patent
Morris

(10) Patent No.: US 11,737,795 B1
(45) Date of Patent: Aug. 29, 2023

(54) SYSTEM AND METHODS FOR ROD INSERTION USING A SCREW TOWER

(71) Applicant: GLOBUS MEDICAL, INC., Audubon, PA (US)

(72) Inventor: Ross Morris, Norristown, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/652,774

(22) Filed: Feb. 28, 2022

(51) Int. Cl.
*A61B 17/88* (2006.01)
*A61B 17/70* (2006.01)

(52) U.S. Cl.
CPC .................. *A61B 17/7082* (2013.01)

(58) Field of Classification Search
CPC ............ A61B 17/7082; A61B 17/7083; A61B 17/7085
USPC .................................................. 606/265, 279
See application file for complete search history.

(56) References Cited

U.S. PATENT DOCUMENTS

| 9,198,692 B1* | 12/2015 | Doose | A61B 17/7032 |
| 2011/0202095 A1* | 8/2011 | Semler | A61B 17/8605 606/305 |
| 2015/0164569 A1* | 6/2015 | Reitblat | A61B 17/708 606/279 |
| 2020/0187988 A1* | 6/2020 | Farmer | A61B 17/708 |
| 2020/0197052 A1* | 6/2020 | Heuer | A61B 17/7085 |
| 2021/0169535 A1* | 6/2021 | Left | A61B 17/7091 |
| 2022/0168024 A1* | 6/2022 | Biedermann | A61B 17/7076 |

* cited by examiner

*Primary Examiner* — Eduardo C Robert
*Assistant Examiner* — David C Comstock

(57) ABSTRACT

A screw tower that is a single-use instrument that attaches to existing screws but remains open along a rod slot to allow for screws to intermesh and prevent interference of adjacent screws during screw and rod insertion. The screw tower interfaces with existing features of the screws to facilitate screw insertion, rod insertion, rod reduction, and locking cap insertion in a percutaneous approach. The tower is broken in half and removed from patient to end with a completed construct.

18 Claims, 10 Drawing Sheets

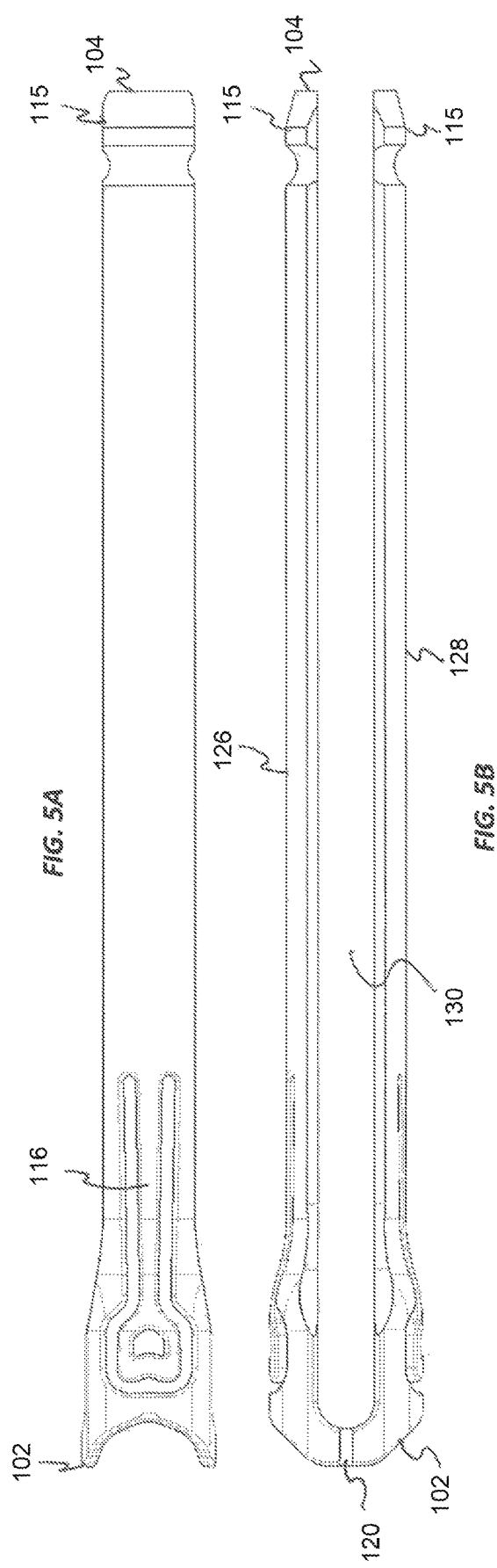

SYSTEM AND METHODS FOR ROD INSERTION USING A SCREW TOWER

FIELD

The present disclosure relates to stabilization systems for fixating adjacent vertebral bodies during spinal surgery, and in particular, spinal surgery fixating adjacent cervical vertebral bodies.

BACKGROUND

Spinal fixation devices may be anchored to specific portions of the vertebra. Such spinal fixation devices may include, for example, a shank portion coupleable to a vertebra, and a head portion having a receiving element. A fixation rod may be seated through the receiving element and locked in place by tightening a locking cap to the head portion. While known spinal fixation systems have proven effective, some rod reducers may be difficult, tiresome, and/or time-consuming to use. For example, in minimally invasive surgery (MIS) applications, percutaneous screws are commonplace in thoracolumbar fixation systems but few options exist for cervical spine applications where a patient's musculature is disrupted greatly in open cases. Most systems for MIS screws are either extended tabs of the screwhead itself or an attachable tower which is similar to a cylinder the entire length of the instrument.

What is needed and provided herein is a single-use instrument that attaches to existing screws but remain open along the rod slot to allow for screws to intermesh and prevent interference of adjacent screws during screw and rod insertion.

SUMMARY

According to some examples of the inventive concepts described herein a screw tower that includes a distal end configured to engage a screw, a proximal end configured to engage instrumentation, a first half and a second half that are connected at the distal end and separately extend to the proximal end, a feature set at the distal end configured to engage a head of a screw. The feature set includes a plurality of chevrons each configured to engage the screw for attachment of the tower to the screw. The feature set further includes a breakpoint configured to allow the first half and the second half to break apart from each other. The screw tower also includes an instrument insertion feature disposed at the proximal end.

In another example, a method of fixating adjacent cervical vertebral bodies. The method includes implanting a screw into a pedicle through an incision, wherein the screw includes a head, and securing a screw tower to the head of the screw. The screw tower includes a distal end configured to engage a screw, a proximal end configured to engage instrumentation, a first half and a second half that are connected at the distal end and separately extend to the proximal end, a feature set at the distal end configured to engage a head of a screw. The feature set includes a plurality of chevrons each configured to engage the screw for attachment of the tower to the screw. The feature set further includes a breakpoint configured to allow the first half and the second half to break apart from each other. The screw tower also includes an instrument insertion feature disposed at the proximal end. The method further includes inserting a rod through the screw tower and into the head of the screw, securing a locking cap to the screw through the screw tower; and breaking the first half and the second half apart at the breakpoint and removing them from the incision.

BRIEF DESCRIPTION OF THE DRAWINGS

The accompanying drawings, which are included to provide a further understanding of the disclosure and are incorporated in and constitute a part of this application, illustrate certain non-limiting examples of inventive concepts. In the drawings:

FIGS. 5A and 5B are perspective views of the screw tower of FIG. 1.

Figure 1:
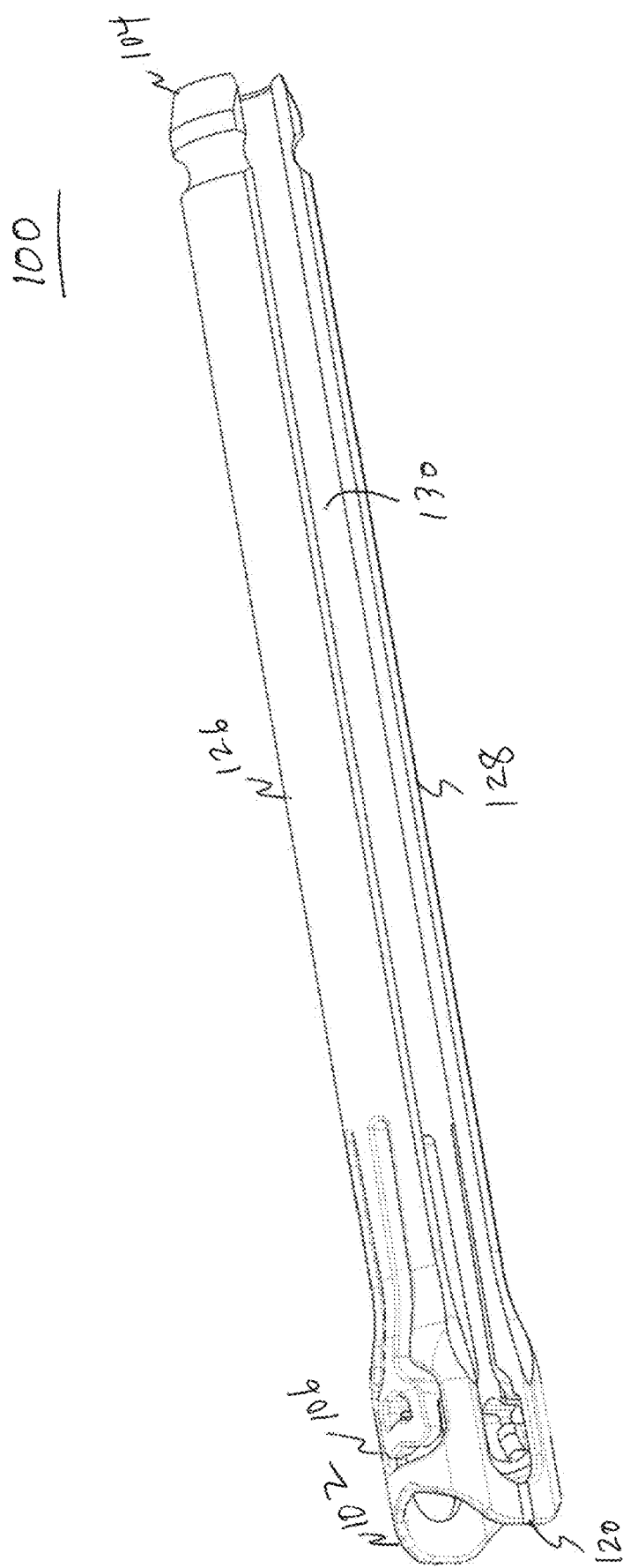
FIG. 1 is a view of an exemplary screw tower consistent with the principles of the present disclosure.

The drawings, which are not necessarily to scale, depict selected examples and are not intended to limit the scope of the disclosure. Although specific features of various examples of the disclosure may be shown in some drawings and not in others, this is for convenience only. The following detailed description is to be read with reference to the drawings, in which like elements in different figures have like reference characters.

DETAILED DESCRIPTION

The present disclosure relates to medical devices and, more particularly, to a MIS screw tower. The present disclose allows for percutaneous insertion of spinal screws using standard, already existing screws. The single-use towers allow for more flexibility with screw size selection in-situ and eases logistics of screw size offerings for a case. The towers include reduction features to assist in locating and positioning a rod without requiring an open incision. Taking this MIS approach into, for example, the cervical spine may preserve more posterior support tissue than an open surgery and may alleviate pain and recovery time in posterior cervical fixation surgeries. These towers may be used with navigation systems.

FIG. 1 illustrates a screw tower 100 consistent with the principles of the present disclosure. Screw tower 100 includes a distal end 102 configured to engage a screw head (e.g., a pedicle screw), a proximal end 104 configured to receive a rod to be attached to the screw head and also configured to engage instrumentation to place the rod, facilitate rod reduction, and to lock the rod in place by a locking cap or another manner of fixation. Two halves 126 and 128 may meet at the distal end and separately extend to the proximal end forming a rod slot 130 in between.

Screw tower 100 may be used in spinal surgeries where the aim is to fixate adjacent vertebral bodies, and in particular, adjacent cervical vertebral bodies. A surgeon may make an incision in patient for spinal surgery. A pedicle screw may be implanted and screw tower 100 may be secured to a head of the screw. A rod may be placed in the pedicle screw, reduction performed, and a locking cap may lock the rod to the pedicle screw. Screw tower 100 may be broken or split apart by separating halves 106 and 108 from each other and removed from the incision leaving the pedicle screw and rod implanted in the patient.

Figure 2B:
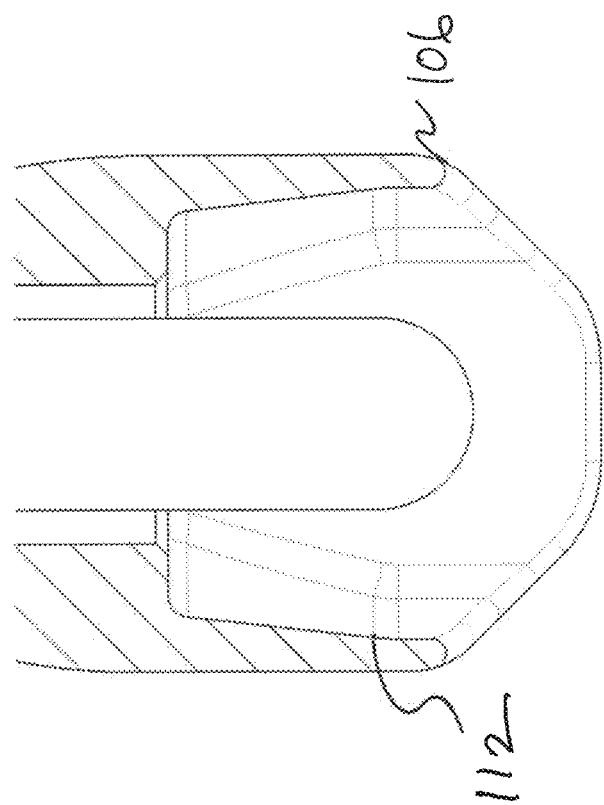
FIGS. 2A and 2B are perspective views of a distal end of the screw tower of FIG. 1.
Figure 2A:
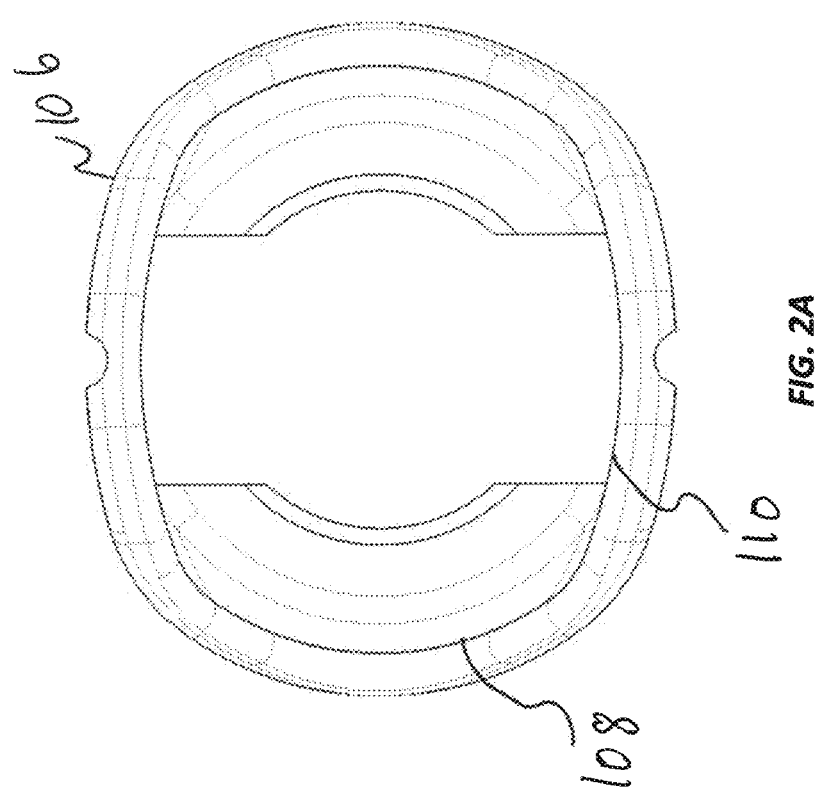

As shown in FIGS. 2A and 2B, tower 100 has of a feature set 106 at distal end 102 that matches a screw head to be implanted. Feature set 106 includes a partial diameter 108 truncated by two larger radii 110 which extend to a height to create a tapered/angled conical surface 112.

Figure 3:
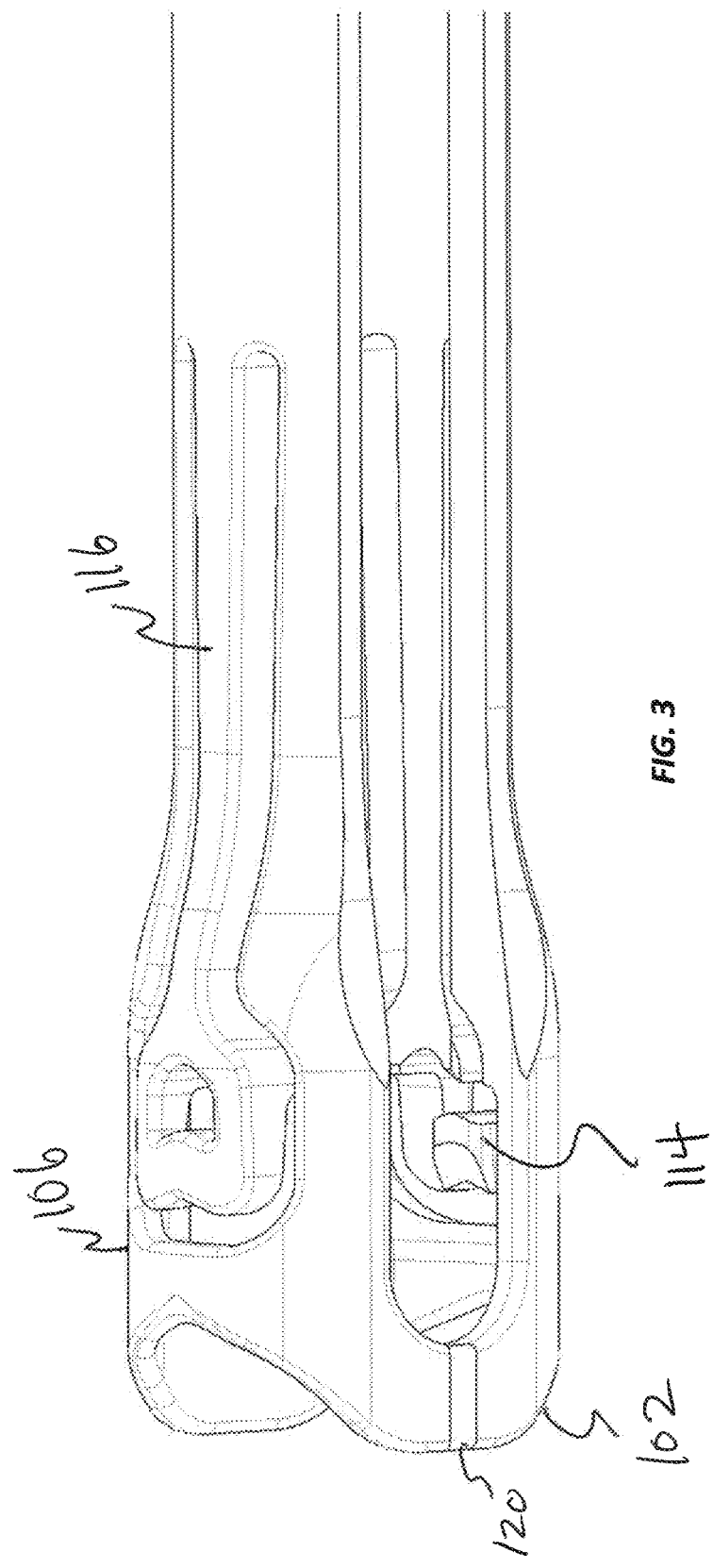
FIG. 3 is a perspective view of a distal end of the screw tower of FIG. 1.
Figure 4B:
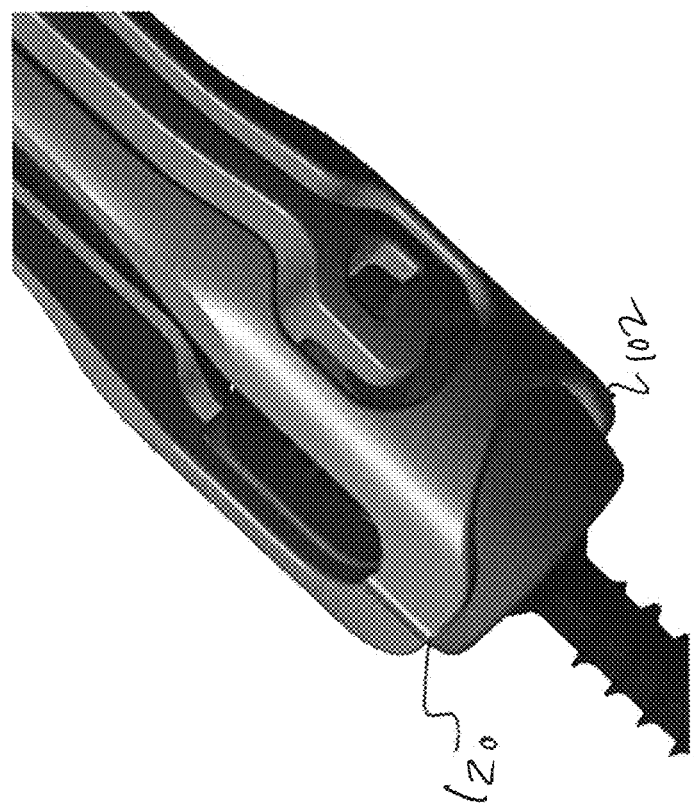
FIGS. 4A and 4B illustrate the screw tower of FIG. 1 engaged with a pedicle screw.
Figure 4A:
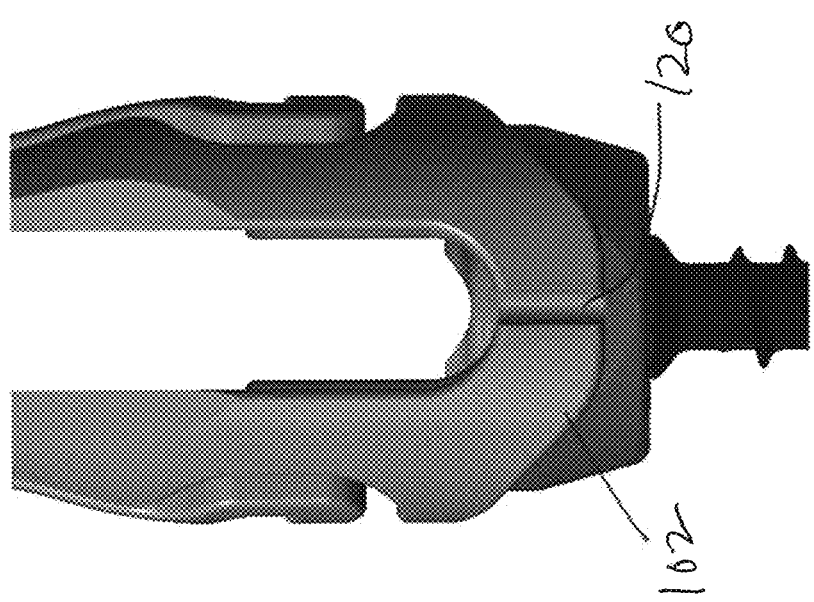
Figure 10:
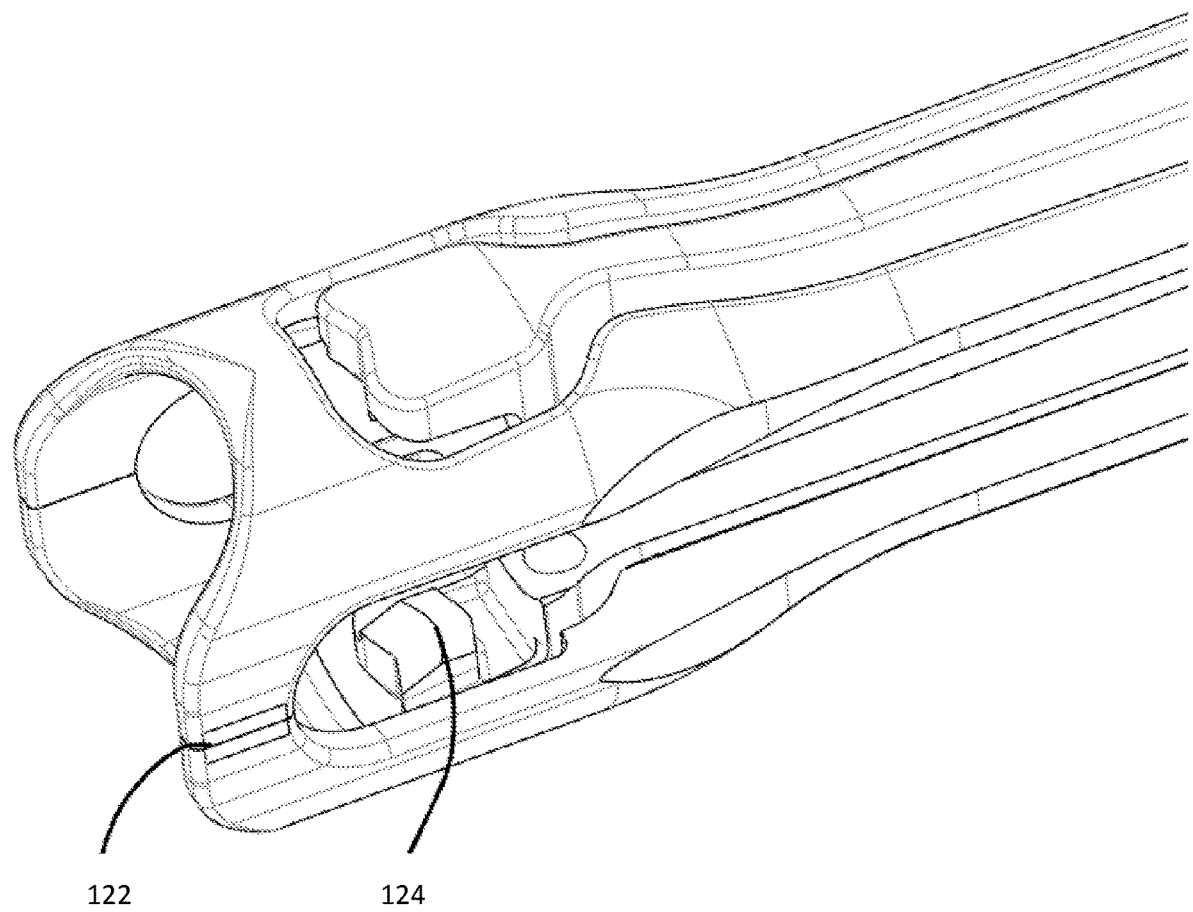
FIG. 10 is a view of an exemplary screw tower consistent with the principles of the present disclosure.

As shown in FIG. 3, within feature set 106 there are components that protrude and interface with components of the screw head. For example, pins or chevrons 114 connect to the chevrons of the screw. A relief cut 116 is configured to allow for chevrons 114 to flex out while a screw is attached. Chevrons 114 return to their interfacing position once the screw is fully inserted into the tower. FIG. 4 illustrates tower 100 engaged with a head of a pedicle screw. The bottom of feature set 106 may be trimmed laterally to reduce the profile of tower 100 and better match any bottom-taper the screw may have as shown in FIG. 4. Tower 100 then extends a distance away from the top of the screw head mating feature clearing out of the incision/wound of the patient being treated. Tower 100 reduces in diameter once it clears the screw head interface to reduce profile and potential interference with adjacent instrumentation. Tower has an instrument insertion feature 115 at proximal end 104 for instruments to attach to and facilitate the reduction of the rod and insertion of a locking cap or set screw. The entire length of tower 100 includes a rod slot 130 slightly larger than a rod slot of the screw head. Tower 100 includes a break point 120 at distal end 102 to facilitate breaking tower 100 into two halves so it may be removed once the rod is inserted and secured into the screw as shown in FIG. 5. Tower 100 may be manufactured as one piece or may be made as two halves that are welded together along or next to the break point feature. FIG. 10 illustrates a screw tower that has been injection molded and welded together at a breakpoint 122. In this design, there is no window in a chevron 124.

Figure 6:
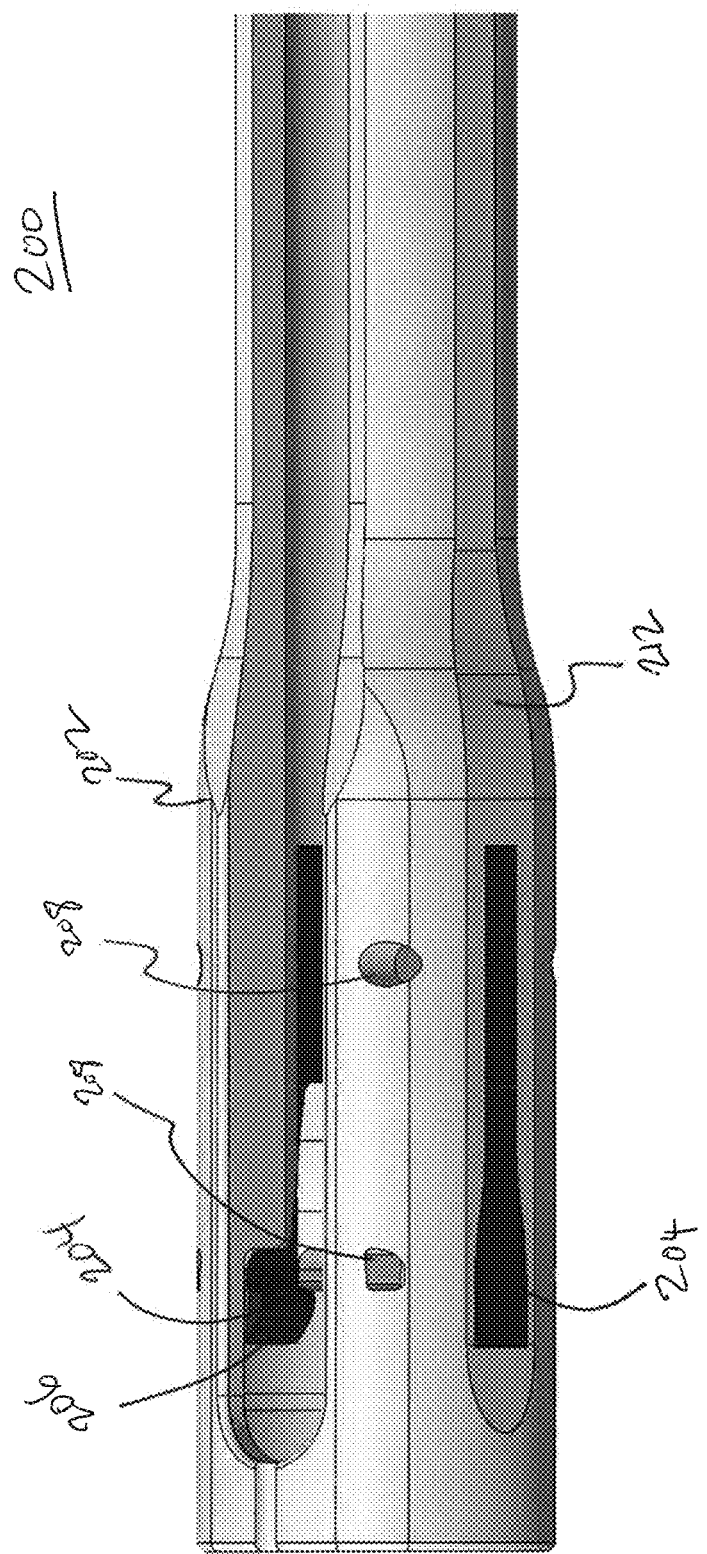
FIG. 6 is a view of an exemplary screw tower consistent with the principles of the present disclosure.
Figure 7C:
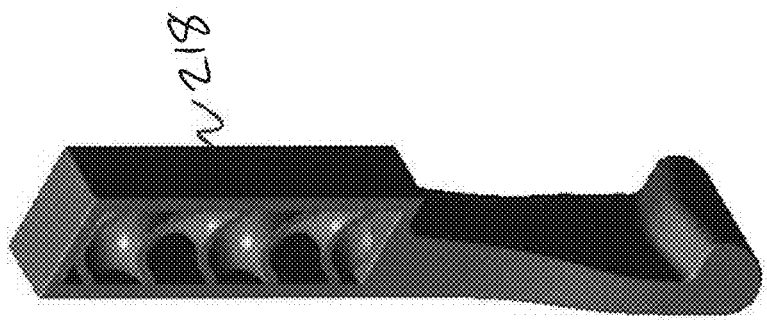
FIGS. 7A, 7B, and 7C illustrate exemplary inserts consistent with the principles of the present disclosure.
Figure 7B:
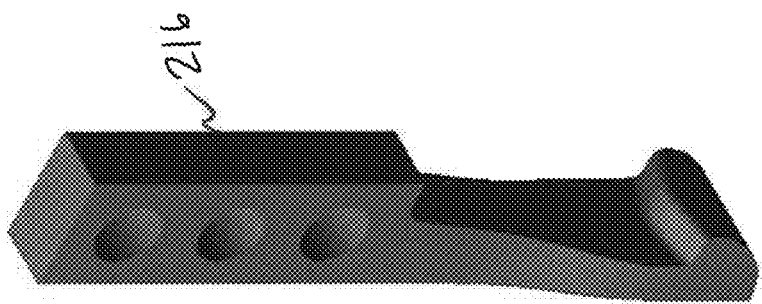
Figure 7A:
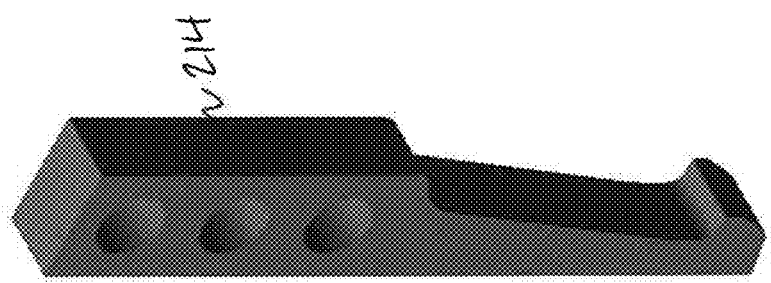

Turning to FIG. 6, tower 200 is illustrated consistent with the principles of the present disclosure. Tower 200 is designed to be injection molded with a polymer 202 over a metallic insert 204, which includes screw attachment mechanism 206. Insert 204 may be bonded or contained within polymer 202 using through holes or a 3D printed lattice structure that polymer 202 can be injected through. A tip 210 of insert 204 is free and can be pushed away by the screw as it is inserted into tower 200 before returning to its nominal, capturing state. Tower 200 have flats 212 along the lateral edges to facilitate the molding process and reduce profile. They may include additional through holes 208 to facilitate the location of the insert during the molding process. FIGS. 7A, 7B, and 7C illustrate three insert 204 designs 214, 216, and 218 which could be stamped, laser cut, milled, or 3D printed.

Figure 8:
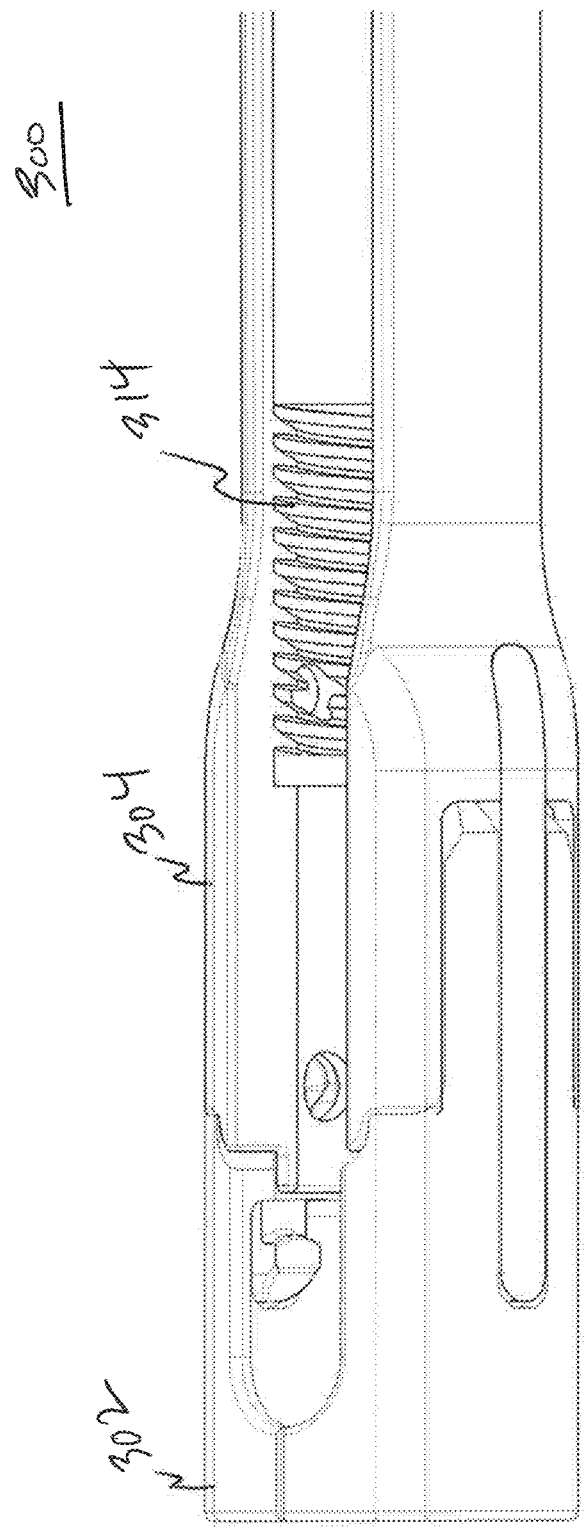
FIG. 8 is a view of an exemplary screw tower consistent with the principles of the present disclosure.
Figure 9:
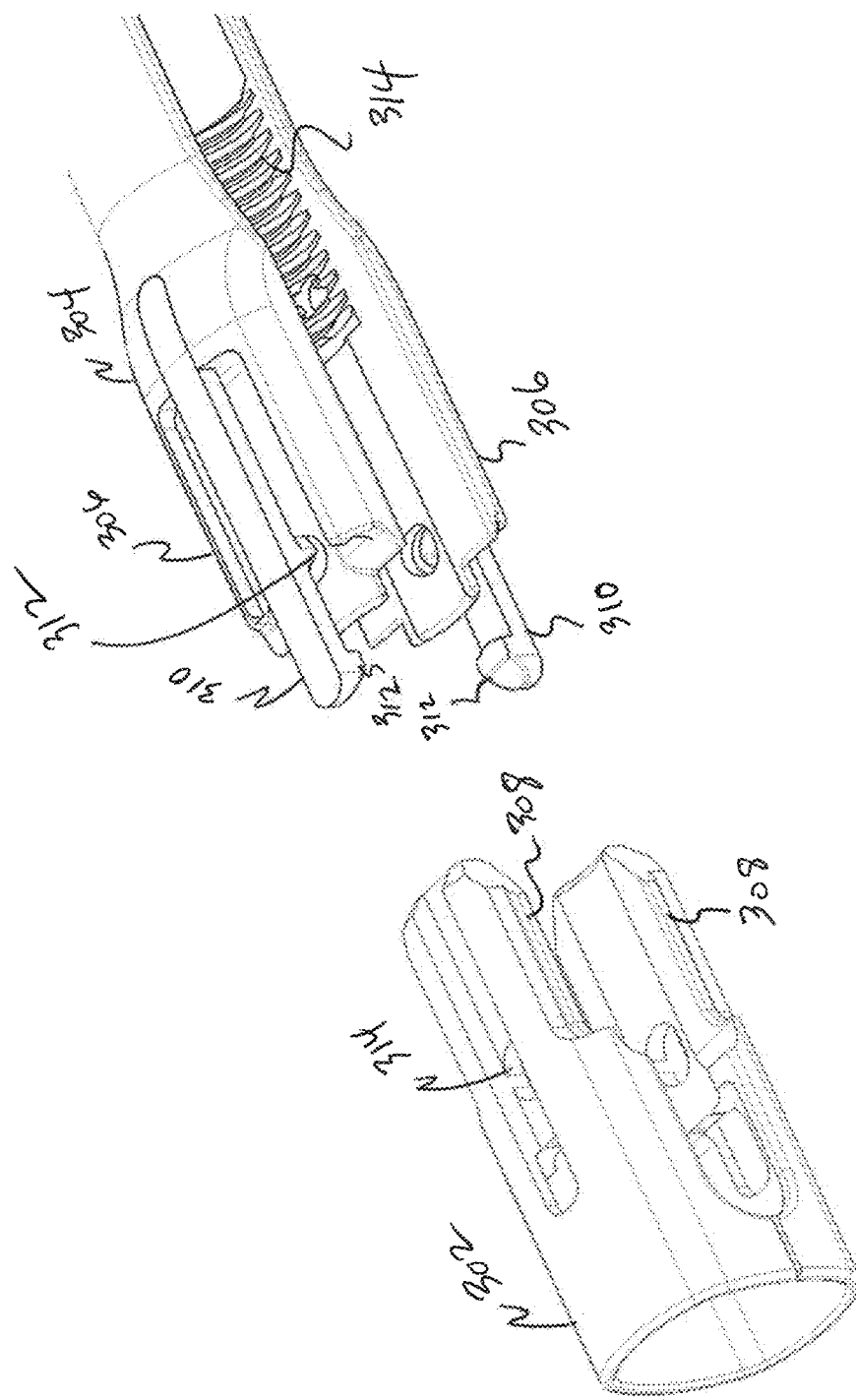
FIG. 9 is a view of an exemplary screw tower consistent with the principles of the present disclosure.

Turning to FIGS. 8 and 9, a tower 300 is illustrated that is consistent with the principles of the present disclosure. Tower 300 contains two segments. A shorter segment 302 (or mini-tower) is a single-use, break away component of tower 300 that attaches to a larger segment 304 via reusable tabs 306. These two segments attach to each other prior to screw attachment. During use, a user would assemble tabs 306 onto shorter segment 302. Tabs 306 attach via a track 308 (t-slot or dovetail) and are retained to segment 302 using a flexible arm 310 which contains a pin 312 that fits into a matching hole 314 of shorter segment 302. With tabs 306 attached, the screw can then be loaded into segment or mini-tower 302 and the screw is retained flexible arms 310 with pins/chevrons 312 that are attached to reusable tabs 306. The most distal chevrons 312 may attach to the screw and the more proximal chevrons 312 may attach segment 304 to segment 302. Segment 302 allows for a cheaper manufacturing process and may be machined or possibly 3D printed. Reusable tabs 306 may have threads 314 intended for a reduction driver instead of a dedicated reduction instrument attachment feature at the end of tower 300.

This written description uses examples to disclose aspects of the disclosure and also to enable a person skilled in the art to practice the aspects, including making or using the above-described systems and executing or performing the above-described methods. Having described aspects of the disclosure in terms of various examples with their associated operations, it will be apparent that modifications and variations are possible without departing from the scope of the disclosure as defined in the appended claims. That is, aspects of the disclosure are not limited to the specific examples described herein, and all matter contained in the above description and shown in the accompanying drawings shall be interpreted as illustrative and not in a limiting sense. For example, the examples described herein may be implemented and utilized in connection with or applied to other examples and applications without departing from the scope of the disclosure. Thus, the aspects of the disclosure are not intended to be limited to the above description and/or accompanying drawings, but are to be accorded the broadest scope consistent with the principles and features disclosed herein.

It is to be understood that the present disclosure is not limited in its application to the details of construction and/or the arrangement of components set forth in the description herein or illustrated in the drawings. For example, in accordance with the principles of the disclosure, any feature described herein and/or shown in the drawings may be referenced and/or claimed in combination with any other feature described herein and/or shown in the drawings. Skilled artisans will recognize the examples provided herein have many useful alternatives and fall within the scope of the disclosure.

The teachings of the present disclosure may be used and practiced in other embodiments and practiced or carried out in various ways. For example, components of the systems and/or operations of the methods described herein may be utilized independently and separately from other components and/or operations described herein. Moreover, the methods described herein may include additional or fewer operations than those disclosed, and the order of execution or performance of the operations described herein is not essential unless otherwise specified. That is, the operations may be executed or performed in any order, unless otherwise specified, and it is contemplated that executing or performing a particular operation before, contemporaneously with, or after another operation is within the scope of the disclosure.

Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When introducing aspects of the disclosure or the examples thereof, the articles "a," "an," "the," and "said" are intended to mean that there are one or more of the elements, unless the context clearly indicates otherwise. References to an "embodiment" or an "example" of the present disclosure are not intended to be interpreted as excluding the existence of additional embodiments or examples that also incorporate the recited features. The phrase "one or more of the following: A, B, and C" means "at least one of A and/or at least one of B and/or at least one of C." The term "and/or" includes any and all combinations of one or more of the associated listed items. It will be understood that although ordinal terms (e.g., "first," "second," "third," etc.) may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Also, it is to be understood that the phraseology and terminology used herein is for the purpose of description and should not be regarded as limiting. Use of the terms "including," "comprising," or "having," and variations thereof, herein is meant to encompass the items listed thereafter and equivalents thereof, as well as additional items. Unless specified or limited otherwise, the terms "mounted," "connected," "supported," and "coupled," and variations thereof, are used broadly and encompass both direct and indirect mountings, connections, supports, and couplings. Further, "connected" and "coupled" are not restricted to physical or mechanical connections or couplings. Moreover, when an element is referred to as being "connected," "coupled," or "responsive," and variations thereof, to another element, it can be directly connected, coupled, or responsive to the other element or intervening elements may be present. In contrast, when an element is referred to as being "directly connected," "directly coupled," or "directly responsive," and variations thereof, to another element, there are no intervening elements present.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A screw tower, comprising:
   a distal end configured to engage a screw;
   a proximal end configured to engage instrumentation;
   a first half and a second half that are connected at the distal end and separately extend to the proximal end;
   a feature set at the distal end configured to engage a head of a screw, wherein the feature set includes a plurality of chevrons each configured to engage the screw for attachment of the tower to the screw, the feature set further including a breakpoint configured to allow the first half and the second half to break apart from each other; and
   an instrument insertion feature disposed at the proximal end
   wherein the feature set includes a partial diameter truncated by two larger radii that extend to a height to form a tapered or conical surface at the distal end.

2. The screw tower of claim 1, wherein each chevron is configured to flex out via a relief cut.

3. The screw tower of claim 1, wherein each of the first half and the second half contain one of the plurality of chevrons.

4. The screw tower of claim 1, wherein the distal end is laterally trimmed to reduce the profile of the tower.

5. The screw tower of claim 1, wherein the first half and the second half form a rod slot.

6. The screw tower of claim 5, wherein a diameter of the distal end is greater than a diameter of the proximal end.

7. The screw tower of claim 5, wherein the size of the rod slot is greater than a screw head rod slot of the screw.

8. The screw tower of claim 1, wherein the first half and second half are manufactured as a single piece configured to break apart at the breakpoint.

9. The screw tower of claim 1, wherein the first half and the second half are welded together at or near the breakpoint.

10. A method of fixating adjacent cervical vertebral bodies, said method comprising:
    implanting a screw into a pedicle through an incision, wherein the screw includes a head;
    securing a screw tower to the head of the screw, wherein the screw tower includes:
      a distal end configured to engage a screw;
      a proximal end configured to engage instrumentation;
      a first half and a second half that are connected at the distal end and separately extend to the proximal end;
      a feature set at the distal end configured to engage a head of a screw, wherein the feature set includes a plurality of chevrons each configured to engage the screw for attachment of the tower to the screw, the feature set further including a breakpoint configured to allow the first half and the second half to break apart from each other; and
      an instrument insertion feature disposed at the proximal end;
    inserting a rod through the screw tower and into the head of the screw;
    securing a locking cap to the screw through the screw tower; and
    breaking the first half and the second half apart at the breakpoint and removing them from the incision
    wherein the feature set includes a partial diameter truncated by two larger radii that extend to a height to form a tapered or conical surface at the distal end.

11. The screw tower of claim 10, wherein each chevron is configured to flex out via a relief cut.

12. The screw tower of claim 10, wherein each of the first half and the second half contain one of the plurality of chevrons.

13. The screw tower of claim 10, wherein the distal end is laterally trimmed to reduce the profile of the tower.

14. The screw tower of claim 10, wherein the first half and the second half form a rod slot.

15. The screw tower of claim 14, wherein a diameter of the distal end is greater than a diameter of the proximal end.

16. The screw tower of claim 14, wherein the size of the rod slot is greater than a screw head rod slot of the screw.

17. The screw tower of claim 10, wherein the first half and second half are manufactured as a single piece configured to break apart at the breakpoint.

18. The screw tower of claim 10, wherein the first half and the second half are welded together at or near the breakpoint.

* * * * *